US009540471B2

(12) United States Patent
Hrabie et al.

(10) Patent No.: US 9,540,471 B2
(45) Date of Patent: Jan. 10, 2017

(54) NITRIC OXIDE-RELEASING DIAZENIUMDIOLATED POLYVINYLPYRROLIDONE-BASED POLYMERS, AND COMPOSITIONS, MEDICAL DEVICES, AND USES THEREOF (71) Applicant: THE UNITED STATES OF AMERICA, AS REPRESENTED BY THE SECRETARY, DEPARTMENT OF HEALTH AND HUMAN SERVICES, Washington, DC (US)

(72) Inventors: Joseph A. Hrabie, Frederick, MD (US); Larry K. Keefer, Bethesda, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/414,765

(22) PCT Filed: Jul. 17, 2013

(86) PCT No.: PCT/US2013/050793
§ 371 (c)(1),
(2) Date: Jan. 14, 2015

(87) PCT Pub. No.: WO2014/014978
PCT Pub. Date: Jan. 23, 2014

(65) Prior Publication Data
US 2015/0166706 A1 Jun. 18, 2015

Related U.S. Application Data (60) Provisional application No. 61/672,486, filed on Jul. 17, 2012.

(51) Int. Cl.
C08F 226/10 (2006.01)
A61K 31/79 (2006.01)

(52) U.S. Cl.
CPC ............ C08F 226/10 (2013.01); A61K 31/79 (2013.01)

(58) Field of Classification Search
None
See application file for complete search history.

(56) References Cited

U.S. PATENT DOCUMENTS

| 6,096,070 | A | 8/2000 | Ragheb et al. |
| 6,270,779 | B1 | 8/2001 | Fitzhugh et al. |
| 6,379,660 | B1 | 4/2002 | Saavedra et al. |
| 6,511,991 | B2 | 1/2003 | Hrabie et al. |
| 6,528,107 | B2 | 3/2003 | Chinn et al. |
| 6,703,046 | B2 | 3/2004 | Fitzhugh et al. |
| 7,776,926 | B1 | 8/2010 | Claude et al. |
| 7,968,664 | B2 | 6/2011 | Hrabie et al. |
| 2004/0180863 | A1 | 9/2004 | Hrabie et al. |
| 2007/0286840 | A1 | 12/2007 | Arnold et al. |
| 2007/0292471 | A1 | 12/2007 | Hrabie et al. |
| 2010/0098733 | A1 | 4/2010 | Stasko |
| 2011/0244001 | A1* | 10/2011 | Mather ............ A61K 47/48976 424/400 |

FOREIGN PATENT DOCUMENTS

| EP | 1 666 047 A1 | 6/2006 |
| WO | WO 00/63462 A1 | 10/2000 |
| WO | WO 2009/064861 A2 | 5/2009 |

OTHER PUBLICATIONS

Arulsamy et al. Journal of Organic Chemistry 2006 71:572-581.*
Perrino et al. European Polymer Journal 2010 46:1557-1562.*
Tarajos et al. Macromolecular Chemistry and Physics 2012 213:529-538.*
Cha et al., "Effects of endothelial cells and mononuclear leukocytes on platelet aggregation," *Haematologia (Budap)*, 30 (2), 97-106 (2000).
Cortivo et al., "Nanoscale particle therapies for wounds and ulcers," *Nanomedicine (Lond)*, 5 (4), 641-656 (2010).
Dashti et al., "Study of the effect of PAPA NONOate on the rate of diabetic wound healing," *African J. Biotech.*, 11 (27), 7088-7093 (2012).
Gries et al., "Inhaled nitric oxide inhibits human platelet aggregation, P-selectin expression, and fibrinogen binding in vitro and in vivo," *Circulation*, 97 (15), 1481-1487 (1998).
Horstmann et al., "Release of nitric oxide from novel diazeniumdiolates monitored by laser magnetic resonance spectroscopy," *Nitric Oxide*, 6 (2), 135-141 (2002).
Hrabie et al., "New Nitric Oxide-Releasing Zwitterions Derived from Polyamines," *J. Org. Chem.*, 58 (6), 1472-1476 (1993).
International Preliminary Report on Patentability, Application No. PCT/US2013/050793, dated Jan. 20, 2015.
International Search Report, Application No. PCT/US2013/050793, dated Oct. 9, 2013.
Jardeleza et al., "The effects of nitric oxide on *Staphylococcus aureus* biofilm growth and its implications in chronic rhinosinusitis," *Int. Forum Allergy Rhinol.*, 1 (6), 438-444 (2011).
Keefer, et al., "'NONOates'" (1-substituted diazen-1-ium-1,2-diolates) as nitric oxide donors: convenient nitric oxide dosage forms," *Methods Enzymol.*, 268, 281-293 (1996).

(Continued)

Primary Examiner — Robert A Wax
Assistant Examiner — Caralynne Helm
(74) Attorney, Agent, or Firm — Leydig, Voit & Mayer, Ltd.

(57) ABSTRACT

Disclosed is a nitric oxide-releasing polyvinylpyrrolidone-based polymer derived from N-vinylpyrrolidone monomer and at least one nitric oxide releasing $N_2O_2^-$ group, in which the $N_2O_2^-$ group is attached to a 2 pyrrolidinone group or a group derived therefrom in the N-vinylpyrrolidone monomer, and the polymer is optionally in combination with a substrate. The NO-releasing polymer can be part of a medical device or pharmaceutical composition and is useful for treating a biological disorder, such as healing a wound, restenosis, and/or promoting angiogenesis.

20 Claims, 3 Drawing Sheets (56) References Cited

OTHER PUBLICATIONS

Kitamura et al., "In vivo nitric oxide measurements using a microcoaxial electrode," *Methods Mol. Biol.*, 279, 35-44 (2004).

Li et al., "Controlled nitric oxide delivery platform based on S-nitrosothiol conjugated interpolymer complexes for diabetic wound healing," *Mol. Pharm.*, 7 (1), 254-266 (2010).

Liu et al, "Heterologous expression of bacterial nitric oxide synthase gene: a potential biological method to control biofilm development in the environment," *Can. J. Microbiol.*, 58 (3), 336-344 (2012).

Lowson et al., "The effect of nitric oxide on platelets when delivered to the cardiopulmonary bypass circuit," *Anesth. Analg.*, 89 (6), 1360-1365 (1999).

Lüscher, "[Thrombocyte-vascular wall interaction and coronary heart disease]," *Schweiz Med. Wochenschr.*, 121 (51-52), 1913-1922 (1991).

Ricciardi et al., "V-PYRRO/NO: an hepato-selective nitric oxide donor improves porcine liver hemodynamics and function after ischemia reperfusion," *Transplantation*, 71 (2), 193-198 (2001).

Riddell et al., "Nitric oxide and platelet aggregation," *Vitam. Horm.*, 57, 25-48 (1999).

Robinson et al., "PVP, A Critical Review of Kinetics and Toxicology of Polyvinylpyrrolidone (Povidone)," *Library of Congress Cataloging-in-Publication Data*, 1-3, 42-43, 46-53, 60-61, 84-87, 144-149 (2009).

Schmidt et al., "Determination of nitrite and nitrate by the Griess reaction." *Methods in Nitric Oxide Research*, 33, 491-497 (1996).

Witte et al., "Nitric oxide enhances experimental wound healing in diabetes," *Br. J. Surg.*, 89 (12), 1594-1601 (2002).

Written Opinion of the International Searching Authority, Application No. PCT/US2013/050793, dated Oct. 9, 2013.

Extended European Search Report, EP Application No. 13819293.5, dated Mar. 3, 2016, 8 pages.

Schoenfisch et al., "Poly(vinylpyrrolidone)-doped nitric oxide-releasing xerogels as glucose biosensor membranes," *Biosensors and Bioelectronics*, 22 (2), 306-312 (Aug. 15, 2006).

\* cited by examiner

NITRIC OXIDE-RELEASING DIAZENIUMDIOLATED POLYVINYLPYRROLIDONE-BASED POLYMERS, AND COMPOSITIONS, MEDICAL DEVICES, AND USES THEREOF

CROSS-REFERENCE TO RELATED APPLICATIONS

This patent application is a U.S. national phase of International Patent Application No. PCT/US2013/050793, filed Jul. 17, 2013, which claims the benefit of U.S. Provisional Patent Application No. 61/672,486, filed Jul. 17, 2012, the disclosures of which are incorporated by reference.

BACKGROUND OF THE INVENTION

The therapeutic efficacy of nitric oxide (NO) has been demonstrated across many different treatment methods. For example, NO has cytotoxic, antiviral, anti-inflammatory, and vasodilator properties. Nitric oxide also has been shown to dramatically reduce thrombocyte and fibrin aggregation/adhesion and smooth muscle cell hyperplasia while promoting endothelial cell growth (Cha et al., Haematologia (Budap), 30(2): 97-106 (2000); Lowson et al., Anesth. Analg., 89(6): 1360-1365 (1999); Riddel et al., Vitam. Horm., 57: 25-48 (1999); Gries et al., Circulation, 97(15): 1481-1487 (1998); and Liischer, Schweiz Med. Wochenschr., 121(51-52): 1913-1922 (1991)). Wounds are known to be deficient in nitric oxide, and as a result, application of NO has been shown to also have beneficial effects on wound healing by, e.g., promoting angiogenesis and tissue remodeling, since NO plays a role in collagen formation. See, e.g., Cortivo et al., Nanomedicine, 5: 641-656 (2010).

Diabetics often suffer from chronic impaired healing, and attempts to use NO therapy have been made. For instance, NO derived from the NO donor molsidomine has been shown to enhance healing in patients with diabetes (Witte et al., Br. J. Surg., 89: 1594-1601 (2002)). S-nitrosothiols have been used as NO donors in polymer blends comprising poly(vinyl methyl ether-co-maleic anhydride) (PVMMA) and poly(N-vinyl-2-pyrrolidone) (PVP) (Li et al., Molecular Pharmaceutics, 7(1): 254-266 (2010)).

However, the delivery of nitric oxide in a stable, nontoxic, and prolonged manner remains a concern. Thus, there remains a desire to provide alternative treatments to improve wound healing and promote angiogenesis with nitric oxide in a manner that is stable, biocompatible, and preferably, bioabsorbable.

BRIEF SUMMARY OF THE INVENTION

The invention described herein provides novel nitric oxide-releasing polyvinylpyrrolidone-based polymers. The polymers of the invention comprise at least one unit derived from an N-vinylpyrrolidone monomer and at least one nitric oxide releasing $N_2O_2^-$ group that is attached, i.e., covalently bonded, to the 2-pyrrolidinone group or a group derived from the 2-pyrrolidinone group of the N-vinylpyrrolidone monomer. The diazeniumdiolated polyvinylpyrrolidone-based polymers can be used in medical devices. The invention also provides methods of using such diazeniumdiolated polyvinylpyrrolidone derivatives. These and other advantages of the present invention, as well as additional inventive features, will be apparent from the description of the invention provided below.

DETAILED DESCRIPTION OF THE INVENTION

The invention provides novel nitric oxide-releasing polyvinylpyrrolidone-based polymers derived from an N-vinylpyrrolidone monomer and at least one nitric oxide releasing $N_2O_2^-$ (—N(O)=N—O$^-$) group that is attached to the 2-pyrrolidinone group or a group derived from the 2-pyrrolidinone group and which are capable of releasing nitric oxide, particularly under physiological conditions. The NO-releasing polymer is optionally part of a composite comprising the NO-releasing polymer in combination with a substrate. These polymers, composites, compositions, and medical devices which include the polymers are useful for treating a biological disorder, such as preventing restenosis and promoting wound healing and angiogenesis. Because the NO-releasing moiety is chemically bound to the polymer, issues relating to the potential toxicity of small NO-donor molecules appearing in the circulatory system are minimized.

Poly(N-vinyl-2-pyrrolidone) (PVP; povidone), is a water soluble and biocompatible polymer that has been used in medicine for over fifty years, and its pharmacology and toxicology have been extensively studied. Insoluble PVP, also known as crospovidone, is a crosslinked PVP typically obtained by treating PVP with alkali hydroxide. Crospovidone is commonly used as a tablet disintegrant and dissolution agent. Copovidone is a water soluble vinylpyrrolidone-vinyl acetate copolymer. Thus, the term "polyvinylpyrrolidone-based polymer" includes any polymer or copolymer derived from N-vinylpyrrolidone, such as povidone, crospovidone, or copovidone. Each of these polyvinylpyrrolidone-based polymers is generally regarded as safe for use in pharmaceutical formulations as they are nontoxic and nonirritating.

The present invention provides a nitric oxide-releasing polyvinylpyrrolidone-based polymer comprising at least one unit derived from N-vinylpyrrolidone monomer and at least one nitric oxide releasing $N_2O_2^-$ group, wherein the $N_2O_2^-$ group is attached to the 2-pyrrolidinone group, which is part of the N-vinylpyrrolidone monomer, or a group derived therefrom. Preferably the polyvinylpyrrolidone-based polymers comprise at least one unit derived from N-vinylpyrrolidone before exposure to nitric oxide. Preferably the $N_2O_2^-$ group is bonded directly, covalently, to the 2-pyrrolidinone group or a moiety derived from the 2-pyrrolidone group, and there is no need for a linking group. In keeping with the invention, the polyvinylpyrrolidone backbone can be diazeniumdiolated with numerous $N_2O_2^-$ groups. The polymer units can also be partially complexed to other pharmaceutically beneficial agents such as iodine (as in povidone-iodine, a widely-used antibacterial) or a small molecule drug. Drugs usefully combined into tablets using PVP are well known to those skilled in the pharmaceutical arts.

Typically each $N_2O_2^-$ group on the polymer also comprises a suitable counterion to balance the charge. Within a single polymer chain, the counterions can be the same or different, but preferably they are the same. Preferably, the counterion is a pharmaceutically acceptable counterion. The only requirement for the pharmaceutically acceptable counterion is biological compatibility in a mammal, such as a human. Biologically acceptable counterions include metal-based counterions, e.g., alkali metals such as sodium ion, potassium ion, lithium ion, and the like; alkaline earth metals such as magnesium ion, calcium ion, and the like; Group III metals such as aluminum ion; Group IV metals such as tin ion; and transition metals, including iron ion, copper ion, manganese ion, zinc ion, cobalt ion, vanadium ion, molybdenum ion, platinum ion, and the like. Non-metal counterions include quaternary ammonium ions. Metal ions that may be considered toxic may, nevertheless, be pharmaceutically acceptable and thus within the scope of the invention if their complexes with the diazeniumdiolates are sufficiently potent pharmacologically and the total concentration of the metal counterion upon dosing is below the toxic threshold of the metal.

In certain embodiments, the polymer comprises at least one monomer unit of formula (I) (an open form of PVP) or formula (II) (a closed form of PVP):

wherein $R^1$ is —$CH_2CH_2CR^4R^5C(O)OR^6$, $R^2$, $R^3$, $R^4$, and $R^5$ are the same or different and each is H or $N_2O_2M$, M is hydrogen or a pharmaceutically acceptable cation, and $R^6$ is H, an unsubstituted or substituted $C_{1-12}$ alkyl, an unsubstituted or substituted $C_{2-8}$ alkenyl, an unsubstituted or substituted $C_3$-$C_6$ cycloalkyl, a substituted or unsubstituted aryl, or $C_{1-12}$ trialkylsilyl, provided at least one of $R^{2-5}$ is $N_2O_2M$. The polymer can comprise any amount and/or combination of the structures set forth in formulae (I) and (II). In some embodiments, the polymer is crosslinked (e.g., crospovidone).

As used herein, unless otherwise specified, the term "alkyl" means a saturated straight chain or branched non-cyclic hydrocarbon having an indicated number of carbon atoms (e.g., $C_1$-$C_{12}$, $C_1$-$C_{10}$, $C_1$-$C_8$, $C_1$-$C_6$, $C_1$-$C_4$, etc.). Representative saturated straight chain alkyls include methyl, ethyl, n-propyl, n-butyl, n-pentyl, n-hexyl, n-heptyl, n-octyl, n-nonyl and n-decyl; while representative saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. An alkyl group can be unsubstituted or substituted.

The term "cycloalkyl," as used herein, means a cyclic alkyl moiety containing from, for example, 3 to 6 carbon atoms, preferably from 5 to 6 carbon atoms. Examples of such moieties include cyclopropyl, cyclobutyl, cyclopentyl, cyclohexyl, and the like.

As used herein, unless otherwise specified, the term "alkenyl group" means a straight chain or branched non-cyclic hydrocarbon having an indicated number of carbon atoms (e.g., $C_2$-$C_8$, $C_2$-$C_6$, $C_2$-$C_4$, etc.) and including at least one carbon-carbon double bond. Representative straight chain and branched alkenyls include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, and the like. Any unsaturated group (double bond) of an alkenyl can be unconjugated or conjugated to another unsaturated group. An alkenyl group can be unsubstituted or substituted.

The term "aryl" refers to an unsubstituted or substituted aromatic carbocyclic moiety, as commonly understood in the art, and includes monocyclic and polycyclic aromatics such as, for example, phenyl, biphenyl, naphthyl, anthracenyl, pyrenyl, and the like. An aryl moiety generally contains from, for example, 6 to 30 carbon atoms, preferably from 6 to 18 carbon atoms, more preferably from 6 to 14 carbon atoms and most preferably from 6 to 10 carbon atoms. It is understood that the term aryl includes carbocyclic moieties that are planar and comprise $4n+2\pi$ electrons, according to Hücker's Rule, wherein n=1, 2, or 3.

As used herein, unless otherwise specified, the term "substituted" means a group substituted by one or more substituents (e.g., 1, 2, 3, 4, 5, 6, etc.), such as, alkyl, alkenyl, alkynyl, cycloalkyl, aroyl, halo, haloalkyl (e.g., trifluoromethyl), haloalkoxy (e.g., trifluoromethoxy), hydroxy, alkoxy, cycloalkyloxy, heterocylooxy, oxo (=O), alkanoyl, aryl, arylalkyl, alkylaryl, heteroaryl, heteroarylalkyl, alkylheteroaryl, heterocyclo, aryloxy, alkanoyloxy, amino, alkylamino, arylamino, arylalkylamino, cycloalkylamino, heterocycloamino, alkanoylamino, aroylamino, aralkanoylamino, substituted alkanoylamino, substituted arylamino, substituted aralkanoylamino, thiol (mercapto), alkylthio, arylthio, arylalkylthio, cycloalkylthio, heterocyclothio, alkylthiono, arylthiono, arylalkylthiono, alkylsulfonyl, arylsulfonyl, arylalkylsulfonyl, sulfonamido (e.g., —$SO_2NH_2$), substituted sulfonamido, nitro, cyano, carboxy, carbamyl (e.g., —$CONH_2$), substituted carbamyl (e.g., —CONH-alkyl, —CONH-aryl, —CONH-arylalkyl, or instances where there are two substituents on the nitrogen selected from alkyl or arylalkyl), alkoxycarbonyl, aryl, substituted aryl, guanidino, substituted or unsubstituted heterocycloalkyl, and substituted or unsubstituted heteroaryl.

In addition, the polymer comprising at least one unit derived from N-vinylpyrrolidone before exposure to nitric oxide can be a copolymer prepared from one or more different comonomers. The copolymer can comprise at least one polymerized comonomer selected from the group consisting of acrylonitrile, styrene, divinylbenzene, 4-methylstyrene, 4-chloromethylstyrene, 4-aminostyrene, 4-chlorostyrene, 4-bromostyrene, 4-vinylphenol, 4-vinylpyridine, 2-vinylpyridine, butadiene, 2-chlorobutadiene, acrylic acid, methacrylic acid, methyl methacrylate, ethyl methacrylate, acrylamide, N-methyl acrylamide, methylacrylonitrile, ethylene, propylene, isoprene, acrolein, methacrolein, 1-glyceryl methacrylate, 2-hydroxyethyl methacrylate, 2-hydroxypropyl methacrylate, vinyl alcohol, allyl alcohol, allyl acetate, vinyl acetate, allylamine, vinylamine, N-methyl vinylamine, N-methyl allylamine, N,N-dimethyl vinylamine, N,N-dimethyl allylamine, isopropenyl acetate, tetrafluorethylene, chlorotrifluoroethylene, dichloroethylene, vinylidene difluoride, vinylchloride, ethylenimine, ethylene oxide, glycidyl acrylate, and glycidyl methacrylate, and/or a repeat unit of an olefin substituted with ester, urethane, amide, carbamate, carbonate, urea, or silane groupings, or any combination thereof. The ester can be formed from, e.g., isophthalate, terephthalate, naphthalene dicarboxylate (e.g., 2,6-, 1,4-, 1,5-, 2,7-, 1,2-, 1,3-, 1,6-, 1,7-, 1,8-, 2,3-, 2,4-, 2,5-, and/or 2,8-substituted), 4,4'-oxybis(benzoate), and/or 5-tert-butyl-1,3-benzene dicarboxylate. The urethane is any suitable polymer formed from a diisocyanate (e.g., diphenylmethane diisocyanate, toluene diisocyanate, hexamethylene diisocyanate, and isophorone diisocyanate) and a polyol (e.g., ethylene glycol, 1,4-butanediol, diethylene glycol, glycerine, trimethylolpropane, sucrose, sorbitol, propylene glycol, and dipropylene glycol). The amide can be, e.g., a peptide, polypeptide, protein, or a synthetic polyamide, such as nylon 6, nylon 66, or nylon 12. The carbamate can be formed from any suitable carbamic acid. The carbonate can be prepared from bisphenol A, if desired. The polyurea can be prepared from a diisocyanate (e.g., diphenylmethane diisocyanate, toluene diisocyanate, hexamethylene diisocyanate, and isophorone diisocyanate) and a polyamine (e.g., ethylene diamine, 1,3-diaminopropane, hexamethylenediamine). The silane can comprise any suitable silane monomer (e.g., an alkene silane such as trimethylsilyl ethylene, trimethylsilyl vinyl alcohol, etc.). The silane preferably forms a polysiloxane, such as polydimethylsiloxane, decamethylcyclopentasiloxane, or hexamethyldisiloxane. Preferably, the copolymer comprises vinyl acetate as a comonomer in addition to a monomer with least one unit derived from N-vinylpyrrolidone (e.g., copovidone).

The comonomers can be present in any suitable ratio in the copolymer. For example, if two monomers, A and B, are used, the resulting copolymer can have a range of weight ratios of A:B, including from about 99:1 to about 1:99. For example, the copolymer can have weight ratios of at least 25:75, at least 50:50, at least 75:25, at least 20:80, at least 30:70, at least 40:60, at least 60:40, at least 70:30, or at least 80:20. The copolymers can be block copolymers, graft copolymers, alternating, or random copolymers. Preferably, they are random copolymers.

In addition, the present invention encompasses polymer blends, in which two or more polymers are physically combined but not chemically linked. Any of the foregoing polymers (or polymers prepared from the monomers above) are suitable for use as a blend with an NO-releasing polymer comprising at least one unit of N-vinylpyrrolidone before exposure to nitric oxide. In an embodiment, the polymers are miscible with one another.

Many polymers and copolymers comprising at least one unit derived from N-vinylpyrrolidone monomer (e.g., povidone, crospovidone, and copovidone) are commercially available, typically in the form of a powder, pellets, beads, granules, fiber, film, sheet, or fabric. Alternatively, suitable polymers and copolymers can be synthetically prepared using standard techniques. For example, a polymer comprising at least one unit derived from N-vinylpyrrolidone monomer can be prepared using free radical polymerization, anionic polymerization, cationic polymerization, Ziegler-Natta catalysis, or metallocene catalysis. Polymer materials of the present invention can take any suitable form, such as a powder, fiber, fabric, membrane, film, gel, coating, salves, creams, ointments, rubber, plastic, or matrix. Typically, the desired form of the polymer or copolymer and/or the desired molecular weight will dictate the polymerization conditions to be used.

The polymers and copolymers, either before or after reaction with NO, can be characterized quantitatively using known methods. For example, molecular weight determinations can be made using gel permeation chromatography (also known as size exclusion chromatography and gel filtration chromatography), matrix-assisted laser desorption/ionization mass spectroscopy (MALDI), light scattering (e.g., low angle and multi angle), small angle neutron scattering (SANS), sedimentation velocity, end group analysis, osmometry, cryoscopy/ebulliometry, and viscometry.

Also, further structural characterization of the polymer can be accomplished using, for example, both solution and solid state nuclear magnetic resonance spectroscopy (NMR), infrared spectroscopy (IR), ultraviolet or ultraviolet-visible (UV-vis) spectroscopy, differential scanning calorimetry (DSC), and mass spectrometry. Nitric oxide content/release can be determined using known techniques such as those described in U.S. Pat. Nos. 6,511,991 and 6,379,660; Keefer, et al., "NONOates (1-Substituted Diazen-1-ium-1, 2 diolates) as Nitric Oxide Donors: Convenient Nitric Oxide Dosage Forms," *Methods in Enzymology,* 28: 281-293 (1996); Horstmann et al., "Release of nitric oxide from novel diazeniumdiolates monitored by laser magnetic resonance spectroscopy," *Nitric Oxide,* 6(2): 135-41 (2002); and Kitamura et al., "In vivo nitric oxide measurements using a microcoaxial electrode," *Methods Mol. Biol.,* 279: 35-44 (2004), which are incorporated herein by reference. In general, the amount of NO produced can be detected and determined by a chemiluminescence method, electrochemical method, absorbance method, and/or the Griess assay (Schmidt et al., *Methods in Nitric Oxide Research*; Feelisch, M.; Stamler, J., Eds.; "Determination of nitrite and nitrate by the Griess reaction." John Wiley and Sons, Ltd.: New York; 1996; pp. 491-497). In addition, nitric oxide assay kits are commercially available.

When a polyvinylpyrrolidone-based polymer comprising at least one unit derived from N-vinylpyrrolidone is reacted with nitric oxide in the presence of a base, preferably a strong base, a diazeniumdiolated polymer forms that is capable of releasing nitric oxide over an extended period of time. The release of nitric oxide can be either in vivo or ex vivo, depending on the ultimate use of the polymer. Preferably, the polymer releases nitric oxide at its intended site for treatment of promoting wound healing and/or angiogenesis. Accordingly, the present invention provides a method of releasing nitric oxide from a nitric oxide-releasing polyvinylpyrrolidone-based polymer comprising at least one unit of N-vinylpyrrolidone and at least one nitric oxide releasing $N_2O_2^-$ group, as described herein. Preferably, the release of NO is under physiological conditions. In one example, the release of NO can occur in vivo or ex vivo at about 37° C. and pH about 7. Also, preferably a polymer of the present invention releases NO over a period of at least one day (i.e., at least about 24 hours), more preferably at least three days (i.e., at least about 72 hours), more preferably at least 5 days (i.e., at least about 120 hours), and most preferably at least 7 days (i.e., at least about 168 hours).

In order to prepare a polyvinylpyrrolidone-based polymer of the present invention, a strong base is used to initiate the reaction. In general, nitric oxide (NO) releasing materials derived, at least in part, from N-vinylpyrrolidone can be prepared as follows: A solution or slurry, as appropriate, of the desired N-vinylpyrrolidone-containing polymer is prepared in a solution of strong base in a solvent contained in a Parr pressure bottle. Nitrogen, argon, or other inert gas is passed through the apparatus and bubbled through the solution for a time sufficient to create an inert environment. The bottle is placed into the reactor system (see, for example, Hrabie et al., *J. Org. Chem.*, 58: 1472 (1993)), further flushed with inert gas, vented, and nitric oxide gas is admitted to a pressure suitable for reacting with the starting material. The reaction is stirred for a time sufficient to allow the reaction to go to completion at room temperature with the addition of NO as needed to maintain the reservoir pressure. Excess NO is then vented, and inert gas is bubbled through the resultant slurry for several minutes. The product is isolated by filtration, washed with solvent (e.g., methanol and/or ethyl ether), and dried in vacuo for several hours or overnight, as appropriate. The products typically are stored in glass jars in a refrigerator until required for experimentation.

Any suitable base can be used; a suitable base is considered a base that can initiate the reaction without itself reacting directly with NO. Preferably, the base is a metal alkoxide of the formula MOR, wherein M is the cation discussed above, and R can be, e.g., an alkyl, aryl, or $C_{1-12}$ trialkylsilyl, as described herein. Preferably R is methyl, t-butyl, or any other R not capable of interacting directly with nitric oxide. Specific bases that can be used include sodium methoxide, potassium isopropoxide, sodium t-butoxide, potassium t-butoxide, lithium t-butoxide, lithium trimethylsilanoate, sodium trimethylsilanoate, and potassium trimethylsilanoate.

Any suitable amount of base can be used relative to the amount of polymer on a moles per mole of monomer unit basis. For example, a range of 1:05 to 1:5 of polymer to base can be used. Specific ratios include 1:0.5, 1:1, 1:1.5, 1:2, 1:2.5, 1:3, 1:3.5, 1:4, 1:4.5, and 1:5. Preferably the ratio is 1:1 or 1:2 PVP monomer units to base on a per mole basis, but the ultimate ratio can be varied as needed to control the number of $N_2O_2^-$ groups in the final product.

If desired, any esters introduced into the film (e.g., —$OR^6$ in the compound of formula (I)) can be altered by transesterification. Suitable groups for transesterification include an unsubstituted or substituted $C_{1-12}$ alkyl, an unsubstituted or substituted $C_{2-8}$ alkenyl, an unsubstituted or substituted $C_3$-$C_6$ cycloalkyl, a substituted or unsubstituted aryl, and $C_{1-12}$ trialkylsilyl.

While not wishing to be bound by any theory, it is believed that in the presence of a base, one or more hydrogen atoms on the 2-pyrrolidinone group are substituted with a diazeniumdiolate group. In a specific example, the following reaction may form at least one or more of the possible polymeric structures:

Of course it is to be understood that not every repeat unit of the polymer is required to have an $N_2O_2^-$ group.

In another aspect, the invention provides a composition, including a pharmaceutical composition, comprising at least one nitric oxide-releasing polyvinyl pyrrolidone-based polymer. Preferably, the pharmaceutical composition further comprises a pharmaceutically acceptable carrier.

One skilled in the art will appreciate that suitable methods of administering a composition comprising a nitric oxide-releasing polyvinylpyrrolidone-based polymer to a mammal, e.g., a mammal such as a human, are known, and, although more than one route can be used to administer a particular composition, a particular route can provide a more immediate and more effective reaction than another route. Pharmaceutically acceptable carriers are also well known to those who are skilled in the art. The choice of carrier will be determined, in part, both by the particular composition and by the particular method used to administer the composition. Accordingly, there are a wide variety of suitable formulations of the pharmaceutical composition of the present invention. Formulations suitable for topical, oral, or parenteral administration preferably comprise at least one NO-releasing polyvinylpyrrolidone-based polymer.

Formulations, including formulations suitable for oral administration, include (a) liquid solutions, such as an effective amount of the diazeniumdiolated polymer dissolved in diluents, (b) capsules, sachets or tablets, each containing a predetermined amount of the active ingredient, as solids or granules, (c) suspensions in an appropriate liquid, and (d) suitable emulsions. Diluents include, for example, water, saline, ethanol, propylene glycol, low molecular weight polyethylene glycol, glycerol, and acetic acid. Tablet forms can include one or more of povidone, crospovidone, lactose, mannitol, cornstarch, potato starch, microcrystalline cellulose, acacia, gelatin, colloidal silicon dioxide, croscannellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

Certain polyvinylpyrrolidone-based polymers, such as povidone, have excellent adhesive properties and safety profile making them good candidates for transdermal applications, oral adhesive gels, and buccal adhesive patches or tablets. A gel formulation can be prepared comprising, for example, a carrier (e.g., water) and at least one of a preservative, a viscosity-increasing agent, and a buffer.

Formulations suitable for parenteral administration include aqueous and non-aqueous solutions, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The dose administered to a mammal, particularly a human, in the context of the present invention should be sufficient to affect a therapeutic response in the mammal over a reasonable time frame. The dose will be determined by the strength of the particular compositions employed (taking into consideration, at least, the rate of NO evolution, the extent of NO evolution, and the bioactivity of any decomposition products derived from the diazeniumdiolates) and the condition of the mammal (e.g., human), as well as the body weight of the mammal (e.g., human) to be treated. The size of the dose also will be determined by the existence, nature, and extent of any adverse side effects that might accompany the administration of a particular composition. A suitable dosage for internal administration is 0.01 to 100 mg/kg per day. A preferred dosage is 0.01 to 35 mg/kg per day. A more preferred dosage is 0.05 to 5 mg/kg per day. A suitable concentration in pharmaceutical compositions for topical administration is 0.05 to 20% (e.g., 0.05 to 15%, 0.02 to 5%, 0.1 to 3%), by weight.

An NO-releasing polyvinylpyrrolidone-based polymer of the present invention can be part of a composite, which comprises the NO-releasing polymer in combination with a substrate. In certain embodiments, the polymer is bound to a substrate. In other words, the diazeniumdiolated polymer can be contacted with a substrate, in which, preferably, the substrate has moieties that allow for chemical bonding of the nitric oxide-releasing polymer. See, for example, U.S. Pat. Nos. 6,703,046, 6,528,107, and 6,270,779, which are incorporated herein in their entirety.

The substrate can be of any suitable biocompatible material, such as metal, glass, natural or synthetic polymer, ceramic, plastic, or rubber. The substrate used in the preparation of the medical device can be derived from any suitable form of a biocompatible material, such as, for example, a powder, dust, an aggregate, an amorphous solid, a sheet, a fiber, a tube, a fabric, or the like.

Metal substrates suitable for use in the invention include, for example, stainless steel, nickel, titanium, tantalum, aluminum, copper, gold, silver, platinum, zinc, Nitinol, Inconel, iridium, tungsten, silicon, magnesium, tin, alloys, coatings containing any of the above, and combinations of any of the above. Also included are such metal substrates as galvanized steel, hot dipped galvanized steel, electrogalvanized steel, annealed hot dipped galvanized steel, and the like. Preferably, the metal substrate is stainless steel.

Glass substrates suitable for use in the invention include, for example, soda lime glass, strontium glass, borosilicate glass, barium glass, glass-ceramics containing lanthanum as well as combinations thereof.

Ceramic substrates suitable for use in the invention include, for example, boron nitrides, silicon nitrides, aluminas, silicas, combinations thereof, and the like.

Polymer substrates suitable for use in the invention include, for example, polyvinylpyrrolidone, acrylics, acrylonitrile-butadiene-styrene, polyacrylonitrile, acetals, polyphenylene oxides, polyimides, polystyrene, polypropylene, polyethylene, polytetrafluoroethylene, polyvinylidene, polyethylenimine, polysaccharides (e.g., cotton, cellulose), polyesters, polyethers, polyamide, polyorthoester, polyanhydride, polyether sulfone, polycaprolactone, polyhydroxybutyrate valerate, polylactones, polyurethanes, polycarbonates, polyethylene terephthalate, as well as copolymers and combinations thereof. Typical rubber substrates suitable for use in the invention include, for example, silicones, fluorosilicones, nitrile rubbers, silicone rubbers, fluorosilicone rubbers, polyisoprenes, sulfur-cured rubbers, butadiene-acrylonitrile rubbers, isoprene-acrylonitrile rubbers, and the like. The substrate could also be a protein, an extracellular matrix component, collagen, fibrin or another biologic agent or a mixture thereof. Silicones, fluorosilicones, polyurethanes, polycarbonates, polylactones, and mixtures or copolymers thereof are preferred plastic or rubber substrates because of their proven bio- and hemocompatability when in direct contact with tissue, blood, blood components, or bodily fluids.

Other suitable substrates include those described in WO 00/63462 and U.S. Pat. No. 6,096,070, and incorporated herein by reference.

The invention provides medical devices which are capable of releasing nitric oxide when in use, but which are otherwise inert to nitric oxide release. In particular, NO-releasing functional groups are bound to a polyvinylpyrrolidone-based polymer derived from N-vinylpyrrolidone monomer with at least one diazeniumdiolate group bound to the 2-pyrrolidinone group which, in turn, is coated on a substrate. Alternatively, the NO-releasing polyvinylpyrrolidone-based polymer can form the medical device itself.

A "medical device" includes any device having surfaces that contact tissue, blood, or other bodily fluids in the course of their use or operation, which are found on or are subsequently used within a mammal. Medical devices include, for example, extracorporeal devices for use in surgery, such as blood oxygenators, blood pumps, blood storage bags, blood collection tubes, blood filters including filtration media, dialysis membranes, tubing used to carry blood and the like which contact blood which is then returned to the patient or mammal. Medical devices also include endoprostheses implanted in a mammal (e.g., a human), such as vascular grafts, stents, pacemaker leads, surgical prosthetic conduits, heart valves, and the like, that are implanted in blood vessels or the heart. Medical devices also include devices for temporary intravascular use such as catheters, guide wires, amniocentesis and biopsy needles, cannulae, drainage tubes, shunts, sensors, transducers, probes and the like which are placed into the blood vessels, the heart, organs or tissues for purposes of monitoring or repair or treatment. Medical devices also include prostheses such as artificial joints such as hips or knees as well as artificial hearts. In addition, medical devices include penile implants, condoms, tampons, sanitary napkins, ocular lenses, sling materials, sutures, hemostats used in surgery, antimicrobial materials, surgical mesh, transdermal patches, and wound dressings/bandages.

In certain preferred embodiments, the medical device is a wound dressing and/or bandage. The wound dressing/bandage can take any suitable form, such as a patch, plaster, bandage, or gauze and can comprise any suitable polymer material, such as a homopolymer, heteropolymer, random copolymer, block copolymer, graft copolymer, mixture or blend of any suitable polymer(s). Suitable polymers include hydrophilic polyurethanes, hydrophilic polyacrylates, co-polymers of carboxymethylcellulose and acrylic acid, poly (hydroxy acids), polyanhydrides, polyorthoesters, polyamides, polyesters, polycarbonates, polyalkylenes (e.g., polyethylene and polypropylene), polyalkylene glycols (e.g., poly(ethylene glycol)), polyalkylene oxides (e.g., polyethylene oxide), polyalkylene terephthalates (e.g., polyethylene terephthalate), polyvinyl alcohols, polyvinyl ethers, polylvinyl esters, polyvinyl halides (e.g., poly(vinyl chloride)), polyvinylpyrrolidone, polysiloxanes, poly(vinyl acetates), polystyrenes, polyurethane copolymers, polysaccharides (e.g., cotton, cellulose), alginates, poly(acrylic acid), poly(acrylic acid) derivatives, acrylic acid copolymers, polymethacrylic acid, polymethacrylic acid derivatives, methacrylic acid copolymers, poly(lactide-co-caprolactone), poly(lactide-co-glycolide), and copolymers thereof and blends thereof. The wound dressing/bandage can be in any suitable physical form, such as a foam, film, woven or non-woven material, hydrogel, ointment, salve, cream, gel matrix, and mixtures and blends thereof.

The wound dressing/bandage can, if desired, include additional additives, such as a water-soluble porogen (e.g., sodium chloride, sucrose, glucose, lactose, sorbitol, xylitol, polyethylene glycol, polyvinylpyrrolidone, polyvinyl alcohol, and mixtures thereof) or at least one additional therapeutic agent (e.g., an antimicrobial compound, an anti-inflammatory agent, a pain-reliever, an immunosuppressant, a vasodilator, a wound healing agent, an anti-biofilm agent, and mixtures thereof).

The NO-releasing polymers of the invention are useful for the treatment of many biological disorders. The present invention provides methods of using a nitric oxide-releasing polyvinylpyrrolidone-based polymer of the invention. In one embodiment, a method of treating a mammal, e.g., a human, with a biological disorder treatable with nitric oxide, is provided. The method comprises administering to the mammal (e.g., human), in need thereof a diazeniumdiolated polymer as described herein, a composite comprising the polymer in combination with a substrate, a composition thereof, or a polymer-containing medical device in an amount sufficient to treat the biological disorder in the mammal (e.g., human). Preferably, the method for treating a biological disorder in a mammal in which dosage with nitric oxide is beneficial comprises administering to a specific location on or within the mammal a medical device comprising a nitric oxide-releasing polyvinylpyrrolidone-based polymer in an amount sufficient to release a therapeutically effective amount of nitric oxide. The treatment can be prophylactic or therapeutic. By "prophylactic" is meant any degree in inhibition of the onset of the biological disorder, including complete inhibition. By "therapeutic" is meant any degree in inhibition of the progression of the biological disorder in the mammal (e.g., human).

In these embodiments, "biological disorder" can be any biological disorder, so long as the disorder is treatable with nitric oxide. Suitable biological disorders include a wound, restenosis, cancer, impotency, platelet aggregation, and a biological disorder due to a genetic defect or infection with an infectious agent, such as a virus, bacterium, fungus or parasite. Moreover, polymers of the present invention can be used to promote the growth of new blood vessels and capillaries in a process known as angiogenesis. In a preferred embodiment, the biological disorder is a wound, restenosis, or infection.

The present invention provides a method for healing a wound in a mammal comprising administering to the mammal an NO-releasing polyvinylpyrrolidone-based polymer described herein, a composite comprising the polymer in combination with a substrate, a composition thereof, or a substrate and/or medical device comprising the polymer to a wound on or within the mammal in an amount sufficient to release a therapeutically effective amount of nitric oxide. The polymer can be administered to a wound (e.g., the surface and/or subsurface of skin) or to a diseased site associated with a dermatological condition (e.g., an ulcer, impetigo, epidermolysis bullosa, pressure sores (also known as pressure ulcers, decubitus ulcers, and bedsores), eczema, neurodermatitis, psoriasis, pruritis, erythema, hidradenitis suppurativa, warts, diaper rash, jock itch, and any combination thereof). The NO-releasing polymer can be applied to intact skin that is diseased or wounded due to a dermatological condition. In a preferred embodiment, the wound is associated with diabetes, such as a diabetic ulcer.

The present invention also provides a method for promoting angiogenesis in a mammal having an adverse condition in need of angiogenesis. The method comprises administering to the mammal an NO-releasing polyvinylpyrrolidone-based polymer described herein, a composite comprising the polymer in combination with a substrate, a composition thereof, or a substrate and/or medical device comprising the polymer to a specific location on or within the mammal in an amount effective to promote angiogenesis in the tissue. Conditions that can be treated in accordance with this method of the invention are characterized by insufficient vascularization (or predisposition thereto) of the affected tissue, i.e., conditions in which neovascularization is needed to achieve sufficient vascularization in the affected tissue, and include, for example, diabetic ulcers, gangrene, surgical or other wounds requiring neovascularization to facilitate healing; Buerger's syndrome; hypertension; ischemic diseases including, for example, cerebrovascular ischemia, renal ischemia, pulmonary ischemia, limb ischemia, ischemic cardiomyopathy, myocardial ischemia, ischemia of tissues such as, for example, muscle, brain, kidney and lung; and other conditions characterized by a reduction in microvasculature. Exemplary tissues in which angiogenesis can be promoted include: hypertension; ulcers (e.g., diabetic ulcers); surgical wounds; ischemic tissue, i.e., a tissue having a deficiency in blood as the result of an ischemic disease including, for example, muscle, brain, kidney, and lung; ischemic diseases including, for example, cerebrovascular ischemia, renal ischemia, pulmonary ischemia, limb ischemia, ischemic cardiomyopathy, and myocardial ischemia. In a preferred embodiment, the tissue can be an ulcer, such as a diabetic ulcer.

For purposes of the present invention, mammals include, but are not limited to, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simioids (monkeys) or of the order Anthropoids (humans and apes). An especially preferred mammal is the human.

The following examples further illustrate the invention but, of course, should not be construed as in any way limiting its scope.

EXAMPLE 1

This example describes the preparation of PVP/NO using about one equivalent of base.

A solution of 10.0 g poly(vinylpyrrolidone) (Sigma-Aldrich; typical MW 55,000; equivalent to approximately 0.09 mole of monomeric vinylpyrrolidone) in 100 mL anhydrous methanol was placed in a 500 mL glass pressure bottle (Parr Instruments Co.) and to this was added 25 mL of 25 wt. % sodium methoxide in methanol solution (Sigma-Aldrich; d=0.945 g/mL; contained 0.109 mole of NaOMe). Argon gas was bubbled through the solution for 5-10 min to remove oxygen, the bottle was placed in the NO reactor system previously described (see Hrabie et al., *J. Org. Chem.*, 58: 1472 (1993)), and the system was further purged with argon. Nitric oxide (NO) gas was admitted to a pressure of 5 atm, and the reaction was stirred for 3 days as the NO pressure slowly fell by about 4 psig. Excess NO was then vented, and inert gas bubbled through the reaction for a few minutes. The reaction mixture was poured into 1.2 L of cold diethyl ether with swirling, the solvent separated from the resulting precipitate by decantation, washed with ether, and dried under vacuum to yield 6.94 g of brittle off-white to yellowish solid easily pulverized to a fine powder. Much of the remaining mass appeared to be present in the precipitate but was lost due to mechanical difficulties in handling the somewhat tacky product.

EXAMPLE 2

This example describes the preparation of PVP/NO using about two equivalents of base.

A solution of 10.0 g poly(vinylpyrrolidone) (as described above) in 100 mL anhydrous methanol was placed in a 500 mL glass pressure bottle as above and to this was added 40 mL of 25 wt. % sodium methoxide in methanol solution (as above; 0.174 mole contained NaOMe). The reaction mixture was treated with NO gas as described above for 5 days. Excess NO was vented, and inert gas was bubbled through the reaction mixture for a few minutes. The reaction mixture was poured into 1.2 L cold diethyl ether with swirling and the solvent separated from the resulting precipitate as before and dried under vacuum to yield 10.24 g of brittle off-white to yellow-brown solid easily pulverized to a fine powder.

EXAMPLE 3

This example describes the preparation of PVP/NO using lithium tert-butoxide as an alternate base.

A partial solution of 1.5 g poly(vinylpyrrolidone) (as described above; equivalent to 0.0137 mole of monomeric vinylpyrrolidone) in 200 mL anhydrous THF was stirred for 1 h at room temperature. To this was added 27.3 mL of 1.0 N lithium tert-butoxide in THF (Sigma-Aldrich, 0.0273 mole contained LiOtBu) resulting in a cloudy suspension, which was placed on the standard NO reactor, flushed with argon, and treated with NO gas at 78 psig for three days with stirring. The NO pressure fell to 73 psig, the reaction was flushed with argon, poured into 1.4 L cold ethyl ether, and allowed to stand in an ice bath for 15 min. The solid was removed by filtration, washed with ether, and dried in a vacuum for 6 h. Yield: 3.46 g off-white hygroscopic powder.

EXAMPLE 4

This example demonstrates the release of NO from the PVP/NO sample of Example 1.

Figure 1:
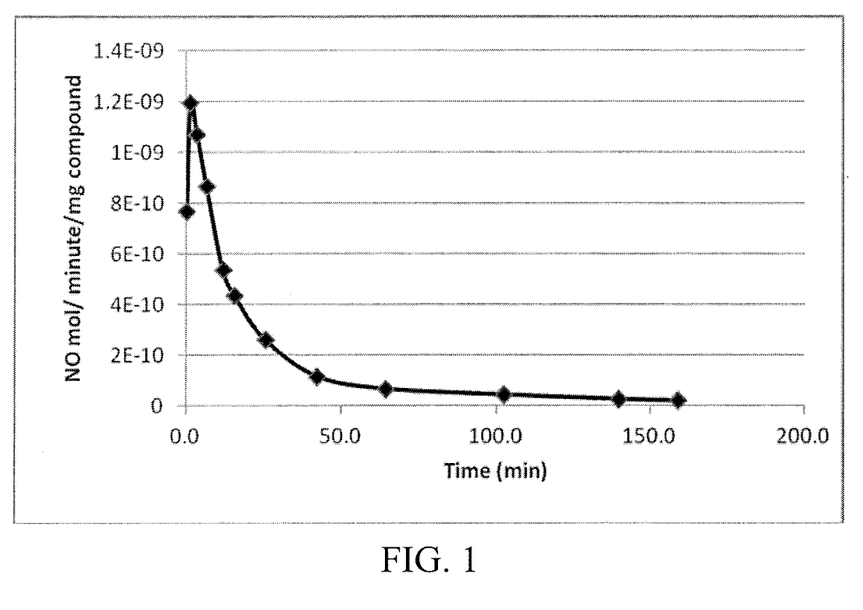
FIG. 1 shows the time course of NO release from the sample of Example 1.

The PVP/NO sample of Example 1 was mixed with pH 7.4 phosphate buffer at 37° C., and the release of NO was monitored by detection of the chemiluminescence generated by treatment of the effluent gas stream with ozone. Integration of the curve shown in FIG. 1 shows a release of $2.57 \times 10^{-8}$ mole NO/mg over about 160 min.

EXAMPLE 5

This example demonstrates the release of NO from the PVP/NO sample of Example 2.

Figure 2:
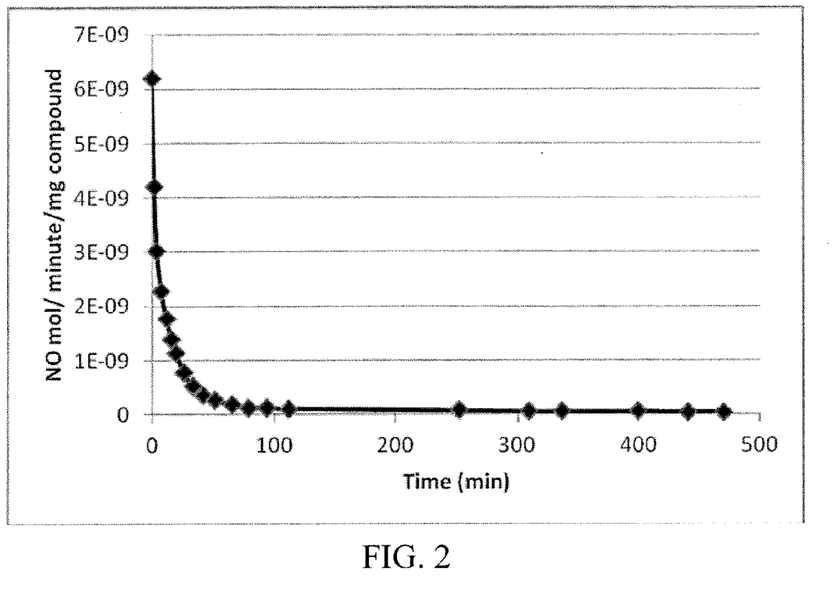
FIG. 2 shows the time course of NO release from the sample of Example 2.

The PVP/NO sample of Example 2 was mixed with pH 7.4 phosphate buffer at 37° C., and the release of NO was monitored by detection of the chemiluminescence generated by treatment of the effluent gas stream with ozone. Integration of the curve shown in FIG. 2 shows a release of $8.43 \times 10^{-8}$ mole NO/mg over about 470 min.

EXAMPLE 6

This example demonstrates the release of NO from the PVP/NO sample of Example 3 compared to the NO release from the poly(acrylonitrile)/NO material.

Figure 3:
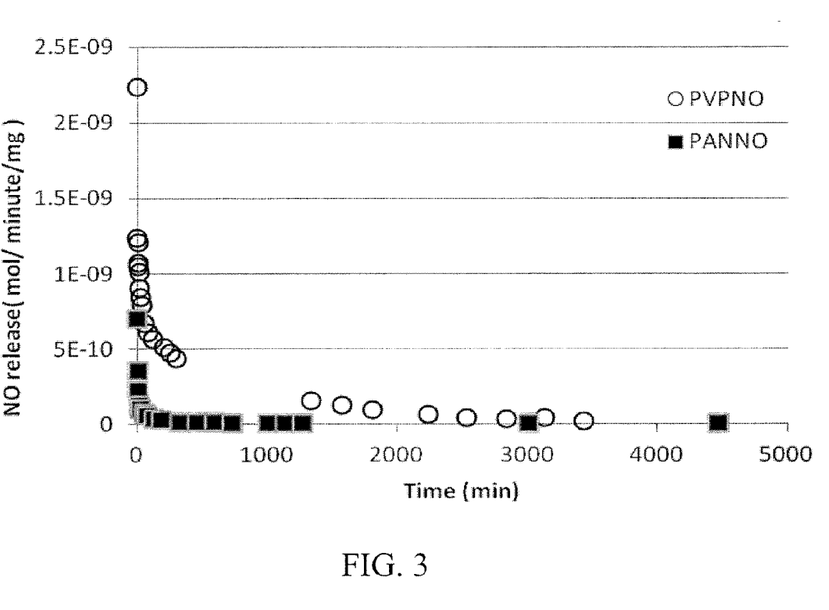
FIG. 3 shows a comparison of the time course of NO release from the sample of Example 3 (○) with the time course of NO release from PAN/NO (■).

The PVP/NO sample of Example 3 was mixed with pH 7.4 phosphate buffer at 37° C., and the release of NO was monitored by detection of the chemiluminescence generated by treatment of the effluent gas stream with ozone. Integration of the curve shown using the diamond-shaped data points in FIG. 3 shows a release of $6.12 \times 10^{-7}$ mole NO/mg over about 3,500 min.

A sample of poly(acrylonitrile)/NO (PAN/NO), prepared according to U.S. Pat. No. 7,968,664, was similarly studied. Integration of the curve shown in using the square-shaped data points in FIG. 3 shows a release of $1.5 \times 10^{-7}$ mole NO/mg over about 4,500 min.

The invention includes the following aspects.

1. A nitric oxide-releasing polyvinylpyrrolidone-based polymer comprising at least one monomer unit derived from N-vinylpyrrolidone and at least one nitric oxide releasing $N_2O_2^-$ group, wherein the $N_2O_2^-$ group is attached to a 2-pyrrolidinone group or a group derived from the 2-pyrrolidinone group of the N-vinylpyrrolidone monomer unit, or a composite comprising the polymer in combination with a substrate.

2. The polymer or composite of aspect 1, wherein the polymer is a copolymer comprising at least one unit derived from N-vinylpyrrolidone.

3. The polymer or composite of aspect 1 or 2, wherein the polymer comprises at least one monomer unit of formula (I) or formula (II)

wherein $R^1$ is $-CH_2CH_2CR^4R^5C(O)OR^6$, $R^2$, $R^3$, $R^4$, and $R^5$ are the same or different and each is H or $N_2O_2M$, M is hydrogen or a pharmaceutically acceptable cation, and $R^6$ is H, an unsubstituted or substituted $C_{1-12}$ alkyl, an unsubstituted or substituted $C_{2-8}$ alkenyl, an unsubstituted or substituted $C_3$-$C_6$ cycloalkyl, a substituted or unsubstituted aryl, or $C_{1-12}$ trialkylsilyl, provided at least one of $R^{2-5}$ is $N_2O_2M$.

4. The polymer or composite of aspect 2 or 3 from the group consisting of acrylonitrile, styrene, divinylbenzene, 4-methylstyrene, 4-chloromethylstyrene, 4-aminostyrene, 4-chlorostyrene, 4-bromostyrene, 4-vinylphenol, 4-vinylpyridine, 2-vinylpyridine, butadiene, 2-chlorobutadiene, acrylic acid, methacrylic acid, methyl methacrylate, ethyl methacrylate, acrylamide, N-methyl acrylamide, methyl acrylonitrile, ethylene, propylene, isoprene, acrolein, methacrolein, 1-glyceryl methacrylate, 2-hydroxyethyl methacrylate, 2-hydroxypropyl methacrylate, vinyl alcohol, allyl alcohol, allyl acetate, vinyl acetate, allylamine, vinylamine, N-methyl vinyl amine, N-methyl allylamine, N,N-dimethyl vinylamine, N,N-dimethyl allylamine, isopropenyl acetate, tetrafluoroethylene, chlorotrifluoroethylene, dichloroethylene, vinylidene difluoride, vinylchloride, ethylenimine, ethylene oxide, tetrahydrofuran, glycidyl acrylate, and glycidyl methacrylate, and/or a repeat unit of an olefin substituted with ester, urethane, amide, carbamate, carbonate, urea, or silane groupings, or any combination thereof.

5. The polymer or composite of aspect 4, wherein the comonomer is vinyl acetate.

6. The polymer or composite of any of aspects 1-3, wherein the polymer is crosslinked.

7. The polymer or composite of any of aspects 1-6 that is a composite.

8. The polymer or composite of aspect 7, wherein the polymer is bound to the substrate in the composite.

9. The polymer or composite of aspects? or 8, wherein the substrate comprises metal, glass, ceramic, polymer, or rubber.

10. A pharmaceutical composition comprising at least one polymer or composite of any of aspects 1-9 and a pharmaceutically acceptable carrier.

11. A medical device comprising the polymer or composite of any of aspects 1-9.

12. The medical device of aspect 11, which is selected from the group consisting of blood oxygenator, blood pump, blood storage bag, blood collection tube, blood filter, dialysis membrane, tubing, vascular graft, stent, pacemaker lead, surgical prosthetic conduit, heart valve, catheter, guide wire, amniocentesis needle, biopsy needle, cannula, drainage tube, shunt, sensor, transducer, probe, artificial joint, artificial heart, penile implant, condom, tampon, sanitary napkin, ocular lens, sling material, suture, hemostat, antimicrobial material, surgical mesh, transdermal patch, and wound dressing or bandage.

13. The medical device of aspect 12, which is a wound dressing or bandage.

14. A method for treating a biological disorder in a mammal in which dosage with nitric oxide is beneficial, comprising administering the polymer or composite of any one of aspects 1-9 to the mammal in an amount sufficient to release a therapeutically effective amount of nitric oxide.

15. A method for treating a biological disorder in a mammal in which dosage with nitric oxide is beneficial, comprising administering the medical device of any one of aspects 11-13 to the mammal in an amount sufficient to release a therapeutically effective amount of nitric oxide.

16. The method of aspect 14 or 15, wherein the biological disorder is selected from the group consisting of a wound, angiogenesis, hypertension, restenosis, cancer, impotency, platelet aggregation, viral or parasitic infection, bacterial infection, and fungal infection.

17. A method for healing a wound in a mammal comprising administering to the mammal the polymer or composite of any one of aspects 1-9 to a wound on or within the mammal in an amount sufficient to release a therapeutically effective amount of nitric oxide.

18. A method for healing a wound in a mammal comprising administering to the mammal the medical device of any one of aspects 11-13 to a wound on or within the mammal in an amount sufficient to release a therapeutically effective amount of nitric oxide.

19. The method of aspect 17 or 18, wherein the wound is associated with a dermatological condition.

20. The method of aspect 19, wherein the dermatological condition is selected from the group consisting of an ulcer, impetigo, epidermolysis bullosa, pressure sore, eczema, neurodermatitis, psoriasis, pruritis, erythema, hidradenitis suppurativa, warts, diaper rash, jock itch, and any combination thereof.

21. A method for promoting angiogenesis in a mammal having an adverse condition in need of angiogenesis, comprising administering to the mammal the polymer or composite of any one of aspects 1-9 in an amount effective to promote angiogenesis.

22. A method for promoting angiogenesis in a mammal having an adverse condition in need of angiogenesis, comprising administering to the mammal the medical device of any one of aspects 11-13 in an amount effective to promote angiogenesis.

23. The method of aspect 20 or 21, wherein the mammal has a condition selected from the group consisting of hypertension, diabetic peripheral vascular disease, gangrene, Buerger's syndrome, a wound, ischemia of the muscle, brain, kidney, lung, heart or limb, severe occlusive and/or obstructive vascular disease, peripheral vascular disease, myocardial ischemia, myocardial infarction, coronary artery disease, cerebral vascular disease, and visceral vascular disease.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A nitric oxide-releasing polyvinylpyrrolidone-based polymer comprising at least one monomer unit derived from N-vinylpyrrolidone and at least one monomer unit selected from the group consisting of formula (I) and formula (II)

or a composite comprising the polymer in combination with a substrate, wherein $R^1$ is —$CH^2CH^2CR^4R^5C(O)OR^6$, $R^2$, $R^3$, $R^4$, and $R^5$ are the same or different and each is H or $N^2O^2M$, M is hydrogen ion or a pharmaceutically acceptable cation, and $R^6$ is H, an unsubstituted or substituted $C_{1-12}$ alkyl, an unsubstituted or substituted $C_{2-8}$ alkenyl, an unsubstituted or substituted $C_3$-$C_6$ cycloalkyl, a substituted or unsubstituted aryl, or $C_{1-12}$ trialkylsilyl, provided at least one of $R^{2-5}$ is $N^2O^2M$ in formula (I) and formula (II).

2. The polymer or composite of claim 1, wherein the polymer comprises at least one polymerized comonomer selected from the group consisting of acrylonitrile, styrene, divinylbenzene, 4-methylstyrene, 4-chloromethylstyrene, 4-aminostyrene, 4-chlorostyrene, 4-bromostyrene, 4-vinylphenol, 4-vinylpyridine, 2-vinylpyridine, butadiene, 2-chlorobutadiene, acrylic acid, methacrylic acid, methyl methacrylate, ethyl methacrylate, acrylamide, N-methyl acrylamide, methylacrylonitrile, ethylene, propylene, isoprene, acrolein, methacrolein, 1-glyceryl methacrylate, 2-hydroxyethyl methacrylate, 2-hydroxypropyl methacrylate, vinyl alcohol, allyl alcohol, allyl acetate, vinyl acetate, allylamine, vinylamine, N-methyl vinylamine, N-methyl allylamine, N,N-dimethyl vinylamine, N,N-dimethyl allylamine, isopropenyl acetate, tetrafluorethylene, chlorotrifluoroethylene, dichloroethylene, vinylidene difluoride, vinylchloride, ethylenimine, ethylene oxide, tetrahydrofuran, glycidyl acrylate, and glycidyl methacrylate, and/or a repeat unit of an olefin substituted with ester, urethane, amide, carbamate, carbonate, urea, or silane groupings, or any combination thereof.

3. The polymer or composite of claim 1, wherein the polymer is crosslinked.

4. The polymer or composite of claim 1 that is a composite.

5. The polymer or composite of claim 4, wherein the polymer is bound to the substrate in the composite.

6. The polymer or composite of claim 4, wherein the substrate comprises metal, glass, ceramic, polymer, or rubber.

7. A pharmaceutical composition comprising at least one polymer or composite of claim 1 and a pharmaceutically acceptable carrier.

8. A medical device comprising a polymer or composite of claim 1.

9. The medical device of claim 8, which is selected from the group consisting of blood oxygenator, blood pump, blood storage bag, blood collection tube, blood filter, dialysis membrane, tubing, vascular graft, stent, pacemaker lead, surgical prosthetic conduit, heart valve, catheter, guide wire, amniocentesis needle, biopsy needle, cannula, drainage tube, shunt, sensor, transducer, probe, artificial joint, artificial heart, penile implant, condom, tampon, sanitary napkin, ocular lens, sling material, suture, hemostat, antimicrobial material, surgical mesh, transdermal patch, and wound dressing or bandage.

10. The medical device of claim 9, which is a wound dressing or bandage.

11. A method for treating a biological disorder in which dosage with nitric oxide is beneficial comprising administering the polymer or composite of claim 1 to the mammal in an amount sufficient to release a therapeutically effective amount of nitric oxide.

12. The method of claim 11, wherein the biological disorder is selected from the group consisting of a wound, angiogenesis, hypertension, restenosis, cancer, impotency, platelet aggregation, viral or parasitic infection, bacterial infection, and fungal infection.

13. A method for treating a biological disorder in which dosage with nitric oxide is beneficial, comprising administering the medical device of claim 8 to the mammal in an amount sufficient to release a therapeutically effective amount of nitric oxide.

14. The method of claim 13, wherein the biological disorder is selected from the group consisting of a wound, angiogenesis, hypertension, restenosis, cancer, impotency, platelet aggregation, viral or parasitic infection, bacterial infection, and fungal infection.

15. A method for healing a wound comprising administering the polymer or composite of claim 1 to a wound on or within the mammal in an amount sufficient to release a therapeutically effective amount of nitric oxide.

16. The method of claim 15, wherein the wound is associated with a dermatological condition.

17. A method for healing a wound in a mammal comprising administering the medical device of claim 8 to a wound on or within the mammal in an amount sufficient to release a therapeutically effective amount of nitric oxide.

18. The method of claim 17, wherein the wound is associated with a dermatological condition.

19. A method for promoting angiogenesis in a mammal having an adverse condition in need of angiogenesis comprising administering to the mammal the polymer or composite of claim 1 in an amount effective to promote angiogenesis.

20. A method for promoting angiogenesis in a mammal having an adverse condition in need of angiogenesis, comprising administering to the mammal the medical device of claim 8 in an amount effective to promote angiogenesis.

* * * * *